(12) United States Patent
Desai et al.

(10) Patent No.: US 6,489,482 B2
(45) Date of Patent: Dec. 3, 2002

(54) PROCESS FOR THE PREPARATION OF NOVEL VINYLIC HINDERED AMINE LIGHT STABILIZERS

(75) Inventors: Shrojal Mohitkumar Desai, Maharashtra (IN); Raj Pal Singh, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/792,275

(22) Filed: Feb. 22, 2001

(65) Prior Publication Data

US 2002/0115754 A1 Aug. 22, 2002

(51) Int. Cl.[7] ............... C07D 211/48; C07D 211/46; C07D 211/58; C07D 211/62
(52) U.S. Cl. ............ 546/242; 546/244; 546/246; 546/248
(58) Field of Search .................. 546/242, 244, 546/246, 248

(56) References Cited

U.S. PATENT DOCUMENTS

| 3,705,166 A | * | 12/1972 | Murayama et al. | .... 260/293.86 |
| 4,014,887 A | * | 3/1977 | Randell et al. | ........ 260/293.84 |
| 4,210,612 A | * | 7/1980 | Karrer | ........................ 525/204 |
| 5,047,489 A | * | 9/1991 | Ravichandran et al. | ..... 526/263 |

OTHER PUBLICATIONS

Singh, R.P., et al. "Photodegradation and Stabilization of Styrene–Butadiene–Styrene Rubber". Journal of Applied Polymer Science, vol. 75 (2000) pp. 1103–1114.

* cited by examiner

Primary Examiner—Patricia L. Morris
(74) Attorney, Agent, or Firm—Ladas & Parry

(57) ABSTRACT

Novel hindered amine light stabilizers of the formula

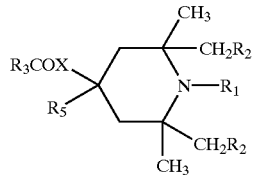

wherein
- $R_1$ is $C_1$ to $C_8$ alkyl, alkoxy, alkylphenyl, hydroxy alkyl, allyl, acyl, or cycloalkyl;
- $R_2$ is hydrogen or methyl;
- $R_3$ is vinyl or $C_{1-4}$ alkyl vinyl;
- $R_4$ is hydrogen, $C_{1-4}$ alkyl or alkyl phenyl;
- $R_5$ is hydrogen or $C_{1-4}$ alkyl; and
- X is O, NH, $C_{1-8}$ linear or branched chain or alkylamino, are prepared from the corresponding 1-unsubstituted, 4-XH-substituted piperidines by first reaction with a carbonyl compound and subsequent reaction with a vinyl group-containing acyl chloride.

11 Claims, No Drawings

PROCESS FOR THE PREPARATION OF NOVEL VINYLIC HINDERED AMINE LIGHT STABILIZERS

FIELD OF INVENTION

This invention relates to a process for the preparation of novel Vinylic Hindered Amine Light Stabilizers (HALS) having general formula (I):

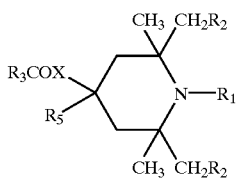

(I)

wherein:
R$_1$ is C$_1$ to C$_8$: alkyl, alkoxy, alkyl phenyl, hydroxy alkyl (all linear and branched), allyl, acyl, cycloalkyl (cyclopentyl, cyclohoxyl or cumyl: linear and branched); R$_2$ is hydrogen or methyl, R$_3$ is Vinyl, C$_1$–C$_4$ vinyl alkyl [H$_2$C=C(R$_4$)C$_1$–C$_4$], R$_4$ is H, C$_1$–C$_4$ alkyl or alkyl phenyl and R$_5$ is H or C$_1$–C$_4$ alkyl, X is O, NH, C$_1$–C$_8$ linear or branched chain or alkylamino.

BACKGROUND OF INVENTION

Monomeric hindered amine light stabilizers are gaining much more importance to stabilize the polyolefins and diene elastomers. Natural and synthetic polymers in common use are susceptible to photo-oxidative degradation upon exposure to natural and artificial weathering. The deterioration of these polymeric materials is mainly due to the UV portion of sunlight reaching the earth surface. The net result of degradation is the loss in the Molecular weight and macroscopic physical properties. Polyolefins and unsaturated synthetic elastomers, being highly sensitive to oxidation, require the addition of stabilizers to provide protection during processing, storage and end-use. The low Molecular weight stabilizers are easily lost from the polymer through evaporation, migration and extraction but, the compatible and mobile stabilizers usually give the best protection. In order to avoid this loss polymer-bound and polymeric stabilizers have been devised. Moreover, since the degradation of a polymer commences from the surface and slowly proceeds into the matrix of the polymeric substrate, the stabilizers are therefore expected to be most potent if they are concentrated at the surface. Therefore, they should be anchored covalently to the polymer surface. Monomeric light stabilizers thus prove to be the best choice to attain the desired photostability.

A discrete literature on the synthesis of the vinylic derivatives of HALS is available; some of these methods are quite trivial and employ complex routes using expensive reagents. Following patents and literature: DE 2950067 (January 1981); DE 2642446 (March 1978); F. E. Karrer, *Markromol. Chem.* 181, 595 (German) 1980, N. S. Prostakov, A. V. Varlomov and G. A. Vasilev, *Khim., Geterotsikl. Soedin.*, 6, 787 (Russian) 1977, JP 53015385 (February 1978); D. V. Sokolov, M. N. Akimova, K. D. Praliev, V. M. Kurilenko, Zh. N. Khlienko and K. M. Moiseeva, *Khim.Farm. Zh.* 11, 47 (Russian) 1977; P. Hrdlovic and S. Chmela, *Int. J. Polym. Mater.*, 13, 245 (1990); J. Pan, Z. Yang, L. Tong, W. Lau, W. Y. Wayne and C. S. Lee, *Polym. Degrad. Stab.* 44, 85, 1994; disclose the preparation and the mechanism of application of HALS derivatives.

Some of the authors have reported vinylic derivatives of HALS as polymerizable light stabilizers wherein, the vinyl group is attached to the hindered nitrogen atom. One of the vinylic derivative of HALS having formula

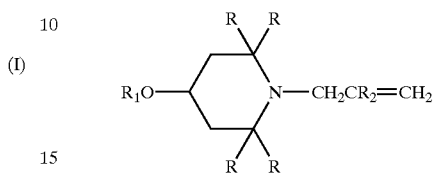

is disclosed in the patent EP 24999145 A1 (December 1987). Upon UV irradiation under atmospheric condition; the hindered nitrogen bearing the vinyl group gets converted into nitroxyl radical (N—O*).

Scheme 1

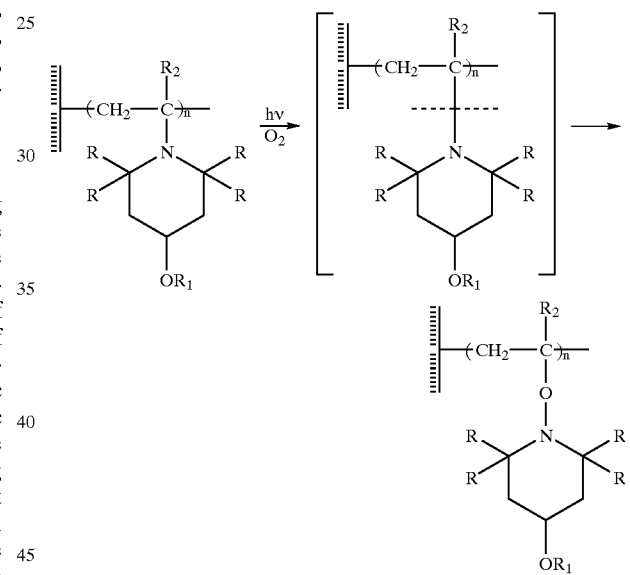

As a result of which the hindered amine moiety gets detached from the covalently bonded vinyl group attached to the surface and is thus prone to be lost due to leaching/extraction/evaporation (shown in the Scheme 1), making it inefficient, The objective of the present invention is therefore, to provide a process for the preparation of novel vinylic HALS, which can the firmly bound to the polymer surface. Moreover, this class of monomeric HALS are known to be compatible with polyolefins, polystyrene and diene elastomers and can even be co-polymerized in a desired proportion to obtain 'in chain' and 'chain end' radical scavengers.

DESCRIPTION OF THE INVENTION

According to the present invention a process for preparation of the said HALS of formula 1, which comprises refluxing the solution of compound having general formula (II)

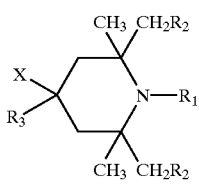
(II)

wherein $R_1$ is hydrogen (H), $R_2$ is hydrogen and methyl, $R_3$ is H, $C_1$–$C_4$ alkyl, X is OH, $NH_2$, $C_1$–$C_8$ alkylhydroxy and alkylamino (linear or branched) an organic solvent containing an carbonyl compound having general formula (III)

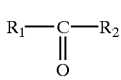
(III)

wherein: $R_1$=$R_2$=H, $C_1$ to $C_8$: alkyl, alkoxy, alkyl phenyl, hydroxy alkyl (linear and branched), allyl, cycloalkyl (cyclopentyl, cyclohexyl or cumyl: linear and branched) in an organic acid for 4–6 hrs, followed by adjusting the pH of the refluxed reaction mixture to 7.0 to 9.0, extracting in an organic solvent and removing the solvent to obtain the compound having formula (IV)

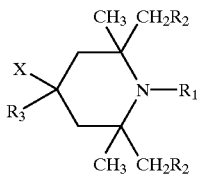
(IV)

wherein: $R_1$ is $C_1$ to $C_8$: alkyl, alkoxy, alkyl phenyl, hydroxy alkyl (linear and branched), allyl, acyl, cycloalkyl (cyclopentyl, cyclohexyl or cumyl: linear and branched); $R_2$ is hydrogen and methyl, $R_3$ is H, $C_1$–$C_4$ alkyl, X is OH, $NH_2$, $C_1$–$C_8$ alkylhydroxy and alkylamino(linear or branched. Reacting the mixture of a catalyst with a compound having formula (IV) in a dry organic solvent in an inert atmosphere adding an organic base under continuous stirring, adding a compound having a general formula (V)

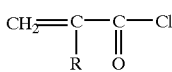
(V)

wherein R is H, $C_1$–$C_4$ alkyl or alkyl phenyl, under stirring and continuing the stirring for a further period of 8 to 12 hrs, quenching with water at a temperature ranging between 0 to 4° C., extracting in an organic solvent, neutralizing the solvent fraction with an inorganic base, evaporating the solvent to obtain the final product. In one of the embodiments of the present invention, the organic acid used for preparing the solution of the compound having formula (II) is selected from formic acid, acetic acid and propanoic acid.

Accordingly the invention provides a process for the preparation of Vinylic Hindered Amine Light Stabilizers having formula

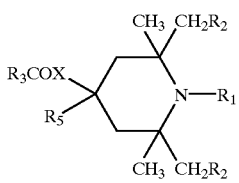
(I)

(I) which comprises refluxing the solution of compound of general formula (II), (II) in an organic solvent containing carbonyl compound of formula (III) for 4–6 hrs, adjusting the pH of the refluxed reaction mixture to 7.0 to 9.0, extracting the reaction product in an organic solvent, removing the solvent to obtain the compound having formula (IV) reacting the above compound of formula (IV) with a catalyst in a dry organic solvent in an inert atmosphere, adding an organic base to the above reaction mixture under continuous stirring, along with a compound having a general formula (V) under stirring and continuing the stirring for a further period of 8 to 12 hrs, quenching the above reaction with water at a temperature ranging between 0 to 4° C., extracting the resultant compound in an organic solvent, neutralizing the solvent fraction with an inorganic base and evaporating the solvent to obtain the final product having formula (I).

In other embodiment of the invention the organic acid used for preparing the solution of the compound having formula (II) is selected from formic acid, acetic acid and propanoic acid.

In one of the other embodiments of the present invention, the carbonyl compound having formula (III) used is selected from the group consisting of formalin, formaldehyde, acetaldehyde, benzaldehyde, methyl ethyl, ketone, methyl benzyl ketone and cyclohexyl methyl ketone.

In yet another embodiments of the present invention, the organic solvent used for extracting the products is selected from the group consisting of used from diethyl ether, dichloromethane, ethyl acetate, and benzene.

In yet another embodiment of the present invention the catalyst used is alkyl substituted amino pyridines selected from the group consisting of N,N-dimethyl aminopyridine, 4-aminopyridine and 2-mercaptobenzoxazole.

In another embodiment the dry organic solvent used to dissolve the catalyst and compound (IV) is selected from the group consisting of dichloromethane, dochloroethane, carbon tetrachloride, cyclohexane, n-hexane and chlorobenzene.

In another embodiment the compound (V) added to react with compound (IV) is selected from the group consisting of acryloyl chloride, methacryloyl chloride, pentenoyl chloride and 3-butenoyl chloride-3-phenyl.

In yet another embodiment the base used is selected from aliphatic and aromatic amine selected from the group consisting from triethyl amine, trimethyl amine, 2,6-lutidine and pyridine.

In yet another embodiment of the invention the inorganic base used to neutralize the solvent fraction containing the product is selected from the group consisting of sodium carbonate, sodium bicarbonate, potassium carbonate.

In yet another embodiment of the present invention wherein the inert gasused is selected from Nitrogen, Argon.

HALS monomers and some of its derivatives may be prepared by any of the methods known in the art including those disclosed in Patents No. JP 53015385 28 (July 1978), Swiss CH 610898 (May 15, 1979), Swiss CH 605927 (October 1978), Brit. GB 1492494 (November 1977) and Literature: T. Tsuchiya and H. Sashida, *Heterocycles*, 14, 1925–8 (1980). All these patents are incorporated herein by reference. HALS namely 2,2,6,6-tetramethyl piperidine and 2,2,6,6-tetramethyl-4-piperidinol may be prepared by synthetic route disclosed by W. B. Lutz, S. Lazams and R. I. Meltzer, *J. Org. Chem.*, 14, 530 (1949). All these patents and literature are incorporated herein by reference.

The process of the present invention is described herein below with references to examples which are illustrative only and should not be construed to limit the scope of the present invention in any manner whatsoever.

EXAMPLE 1

Synthesis of 1,2,2,6,6-Pentamethy-4-piperidinol 1,2,2,6,6-pentamethy-4-piperidinol was synthesized upon reductive-amination of 2,2,6,6-tetramethy-4-piperidinol. A mixture of 2,2,6,6-tetramethyl]-piperidinol (3.55 g, 0.02 M), 37% formalin (3.3 mL) and 1 mL formic acid was heated under a reflux condensor on the steam bath for 5 h. The reaction mixture was made basic with (1.0 M) potassium hydroxide solution and the product was extracted with ether (5×50 mL). The combined extract was washed with saturated solution of potassium carbonate (2×20 mL) and dried over anhydrous magnesium sulfate and finally the solvent was evaporated under vacuum. The residue was then sublimed at 0.05 mm, bath temperature 85° C. The white sublimate weighed 3.5 g to give 91% yield, mp=72–74° C.

EXAMPLE 2

Synthesis of 1,2,2,6,6-Pentamethy Piperidinyl-4-acrylate

This model compound was synthesized strictly under dry and inert reaction conditions, 1,2,2,6,6-pentamethy-4-piperidinol (1.0 g, 0.00588 M) was taken in a two necked 25 mL capacity round bottom flask (RB) along with 4-dimethyl aminopyridine (DMAP) (30 mg, 0.245 mM) and was kept under nitrogen atmosphere. Dry dichloromethane (15 mL) was injected into the tightly closed RB through the rubber septum, followed by dry triethyl amine (TEA) (1.2 mL, 0.0087 M). This reaction mixture was stirred for 10 minutes at room temperature followed by the addition of acryloyl chloride (0.55 mL, 0.0069 M) with stirring. The reaction mixture was agitated at room temperature for 10 hrs. This reaction mixture was then quenched in ice water, and the product was extracted in dichloromethane (4×25 mL). The combined extract was given (2×20 mL) washes of saturated sodium bicarbonate solution and finally dried over anhydrous magnesium sulfate. The solvent was evaporated under vacuum at 38° C. over a rotavapor. The product was found to be almost pure (97.8% by Gas Chromatography). The TLC didn't show any spot of either the starting material or the catalyst (DMAP). The 1,2,2,6,6-pentamethy piperidinyl-4-acrylate yield was 1.11 g (85%).

EXAMPLE 3

Synthesis of 1,2,2,6,6-Pentamethyl Piperidinyl-4-acrylamide

This compound was synthesized strictly under dry and inert reaction conditions. 1,2,2,6,6-pentamethy-4-aminopiperidine (1.0 g, 0.00584 M) was taken in a two necked 25 mL capacity RB along with 4-dimethyl aminopyridine (DMAP) (35 mg 0.28 mM) and was kept under nitrogen atmosphere. Dry dichloromethane (15 mL) was injected into the tightly closed RB through the rubber septum, followed by dry triethyl amine (TEA) (1.2 mL, 0.0087M). This reaction mixture was stirred for 10 minutes at 10–12° C. followed by the gradual addition of acryloyl chloride (0.55 mL 0.0069 M) with stirring at 0–5° C., The reaction mixture then, was allowed to stir at room temperature for approximately 10 hrs. This reaction mixture was then quenched in ice water, and the product was extracted in dichloromethane (4×25 mL). The combined extract was given (2×20 mL) washes of saturated potassium bicarbonate solution and finally dried over anhydrous magnesium sulfate. The solvent was evaporated under vacuum at 38° C. over a rotavapor. The crude product was found to be 89.8% pure (by Gas Chromatography). It was further purified by column chromatography. The yield of 1,2,2,4,4-pentamethy piperidinyl-4-acrylamide after purification was found to be 1.15 g (88%).

EXAMPLE 4

Synthesis of 1-Tert-pentyl-2,2,6,6-tetramethy Piperidinyl-4-acrylate 1-tert-pentyl-2,2,6,6-tetramethy-4-piperidinol was synthesized strictly under dry and inert reaction conditions. 1-tert-pentyl-2,2,6,6-tetramethy-4-piperidinol (2.0 g, 0.00876 M) was taken in a two necked 50 ml capacity round bottom flask (RB) along with 4-dimethyl aminopyridine (DMAP) (53.5 mg, 0.437 mM) and was kept under nitrogen atmosphere, Dry dichloromethane (25 mL) was injected into the tightly closed RB through the rubber septum, followed by dry tiethyl amine (TEA) (1.83 mL, 0.0131 M). This reaction mixture was stirred for 10 minutes at room temperature followed by the addition of acryloyl chloride (0.85 mL, 0.0105 M) with stirring. The reaction mixture was agitated at room temperature for 10 hrs. This reaction mixture was then quenched in ice water, and the product was extracted in dichloromethane (4×25 mL). The combined extract was given (2×20 mL) washes of saturated potassium bicarbonate solution and finally dried over anhydrous magnesium sulfate. The solvent was evaporated under vacuum at 38° C. over a rotavapor and the product was found to be almost pure. The TLC didn't show any spot of either the starting material or the catalyst (DMAP). The yield of product was 2.10 g (85%).

EXAMPLE 5

Synthesis of 1-Allyl-2,2,6,6-tetramethy Piperidinyl-4-acrylate 1-allyl-2,2,6,6-tetramethy-4-piperidinol (1.5 g, 0.00756 M) was taken in a two necked 50 ml capacity round bottom flask (RB) along with 4-dimethyl aminopyridine (DMAP) (46.2 mg, 0.387 mM) and was kept under nitrogen atmosphere. Dry n-hexane (25 mL) was injected into the tightly closed RB through the rubber septum, followed by dry triethyl amine (TEA) (1.73 mL, 0.0124 M). This reaction mixture was stirred for 10 minutes at 10° C. followed by the addition of acryloyl chloride (0.79 mL, 0.0098 M) with stirring at 0° C. The reaction mixture was agitated initially for 3 hrs at 5° C. and for the remaining period at room temperature for approximately 9 hrs under nitrogen atmosphere. This reaction mixture was then quenched in ice water, and the product was extracted in n-hexane (4×25 mL). The combined extract was given (2×20 mL) washes of saturated potassium bicarbonate solution and finally dried over anhydrous magnesium sulfate. The solvent was evaporated under vacuum at 38° C. over a rotavapor. The crude yield of 1-allyl-2,2,6,6-tetramethy piperidinyl-4-acrylate was 1.65 g (86.5%).

EXAMPLE 6

Synthesis of 1-Methylcylcohexyl-2,2,6,6-tetramethyl Piperidinyl-4-acrylate

This desired compound was synthesized strictly under dry and inert reaction conditions. 1-methylcylcohexyl-2,2,6,6-tetramethyl piperidinol (1.0 g, 0.00588 M) was taken in a two necked 25 ml capacity round bottom flask (RB) along with 4-dimethyl aminopyridine (DMAP) (30 mg, 0.245 mM) and was kept under nitrogen atmosphere. Dry dichloromethane (15 mL) was injected into the tightly closed RB through the rubber septum, followed by dry triethyl amine (TEA) (1.2 mL, 0.0087 M). This reaction mixture was stirred for 10 minutes at room temperature followed by the addition of acryloyl chloride (0.55 mL, 0.0069 M) with stirring at 5° C. The reaction mixture was agitated at room temperature for 10 hrs. This reaction mixture was then quenched in ice water, and the product was extracted in dichloromethane (4×25 mL). The combined extract was given (2×20 mL) washes of saturated potassium bicarbonate solution and finally dried over anhydrous magnesium sulfate. The solvent was evaporated under vacuum at 38° C. over a rotavapor. The product was found to be almost pure (97.8% by Gas Chromatography). The TLC didn't show any spot of either the starting material or the catalyst (DMAP). The yield of 1-methylcylcohexyl-2,2,6,6-tetramethyl piperidinyl-4-acrylate was found to be 1.003 g (82.8%).

EXAMPLE 7

Synthesis of 1-Ethylphenyl-2,2,6,6-tetramethyl Piperidinyl-4-acrylate 1-ethylphenyl-2,2,6,6-tetramethyl4-piperidinol (2.0 g, 0.0076 M) was taken in a two necked 50 mL capacity round bottom flask (RB) along with 4-dimethyl aminopyridine (DMAP) (46.5 mg, 0.387 mM) and was kept under nitrogen atomsphere. Dry carbon tetrachloride (25 mL) was injected into the tightly closed RB through the rubber septum, followed by dry pyridine (0.907 mL, 0.0112M). This reaction mixture was stirred for 10 minutes at 10–12° C. followed by the addition of acryloyl chloride (0.75 mL, 0.0098 M) with stirring at 5° C. The reaction mixture was agitated at room temperature for approximately 13 hrs. This reaction mixture was then quenched in ice water, and the product was extracted in ethyl acetate (4×25 mL). The combined extract was given (2×20 mL) washes of saturated potassium bicarbonate solution and finally dried over anhydrous magnesium sulfate. The solvent was evaporated under vacuum at 38° C. The yield of 1-ethylphenyl-2,2,6,6-tetramethyl piperidinyl-4-acrylate was 1.93 g (80%).

EXAMPLE 8

Synthesis of 1-Methyl-2,6-diethyl-2,6-methyl Piperidinyl 1-4-acrylate 1-methyl-2,6-diethyl-2,6-di methyl-4-piperidinol (2.5 g, 0.0125 M) was taken in a two necked 50 mL capacity round bottom flask (RB) along with 4-dimethyl aminopyridine (DMAP) (76.5 mg, 0.625 mM) and was kept under nitrogen atomsphere. Dry dichloromethane (35 mL) was injected into the tightly closed RB through the rubber septum, followed by dry triethyl amine (TEA) (2.6 mL, 0.0187 M). This reaction mixture was stirred for 10 minutes at room temperature followed by the addition of acryloyl chloride (0.75 mL, 0.0098 M) with stirring at 5° C. The reaction mixture was agitated at room temperature for 10 hrs. This reaction mixture was then quenched in ice water, and the product was extracted in dichloromethane (4×25 mL). The combined extract was given (2×20 mL) washes of saturated potassium bicarbonate solution and finally dried over anhydrous magnesium sulfate. The solvent was evaporated under vacuum at 38° C. The 1-methyl-2,6-diethyl-2,6-dimethyl piperidinyl-4-acrylate was found to be almost pure and its yield was 2.85 g (90%).

EXAMPLE 9

Synthesis 1-Methyl-2,6-diethyl-2,6-dimethyl Piperidinyl-4-acryl amide 1-methyl-2,6-diethyl-2,6-dimethyl-4-aminopiperidine (2.0 g, 0.010 M) was taken in a two necked 50 mL capacity round bottom flask (RB) along with 4-dimethyl aminopyridine (DMAP) (61.5 mg, 0.5 mM) and was kept under nitrogen atmosphere. Dry chlorobenzene (35 mL) was injected into the tightly closed RB through the rubber septum, followed by dry triethyl amine (TEA) (1.96 mL, 0.0141 M). This reaction mixture was stirred for 10 minutes at 15° C. followed by gradual addition of acryloyl chloride (0.75 mL, 0.0098 M) with stirring at 0–5° C. The reaction mixture was initially agitated at 5° C. for 3 hrs followed by stirring at room temperature for 10 hrs. This reaction mixture was then quenched in ice water, and the product was extracted in diethylether (4×25 mL). The combined extract was given (2×20 mL) washes of saturated potassium bicarbonate solution and finally dried over anhydrous magnesium sulfate. The solvent was evaporated under vacuum at 38° C. over a rotavapor. The product was found to be 85% pure and was further purified by column chromatography under nitrogen atmosphere. The yield of the reaction was 2.03 g (81%).

EXAMPLE 10

Synthesis of 1,2,2,4,6,6-Hexamethyl Piperidinyl-4-acrylate 1,2,2,4,6,6-hexamethyl piperidinol (1.5 g, 0.0081 M) was taken in a two necked 50 mL capacity round bottom flask (RB) along with 4-dimethyl aminopyridine (DMAP) (49.5 mg, 0.405 mM) and was kept under nitrogen atomsphere. Dry dichloromethane (30 mL) was injected into the tightly closed RB through the rubber septum, followed by dry triethyl amine (TEA) (1.7 mL, 0.0121 M). This reaction mixture was stirred for 10 minutes at room temperature followed by the addition of acryloyl chloride (0.77 mL, 0.0097 M) with stirring at 5° C. The reaction mixture was agitated at room temperature for 10 hrs. This reaction mixture was then quenched in ice water, and the product was extracted in dichloromethane (4×25 mL). The combined extract was given (2×20 mL) washes of saturated potassium bicarbonate solution and finally dried over anhydrous magnesium sulfate. The solvent was evaporated under vacuum at 38° C. The product was found to be almost pure (98% pure by GC). 1,2,2,4,6,6-hexamethyl piperidinyl-4-acrylate obtained at the end of the reaction was 1.77 g (91.4%).

EXAMPLE 11

Synthesis of 1,2,2,4,6,6-Hexamethyl Peridinyl-4-acryamide 1,2,2,4,6,6-hexamethyl-4-aminopiperidine (2.0 g, 0.0108 M) was taken in a two necked 50 mL capacity round bottom flask (RB) along with 4-dimethyl aminopyridine (DMAP) (66.5 mg, 0.543 mM) and was kept under nitrogen atmosphere. Dry dichloromethane (30 mL) was injected into the tightly closed RB through the rubber septum, followed by dry triethyl amine (TEA) (2.1 mL, 0.015 M). This reaction mixture was stirred for 10 minutes at 15° C. followed by the gradual addition of acryloyl chloride (0.86 mL, 0.01087 M) with stirring at 0–5° C. initially for 2 hrs. The reaction mixture was then agitated at room temperature for 9 hrs. This reaction mixture was then quenched in ice water, and the product was extracted in dichloromethane (4×25 mL). The combined extract was given (2×20 mL) washes potassium bicarbonate solution and finally dried over anhydrous magnesium sulfate. The solvent was evaporated at 38° C. under vacuum over rotavapor. The product was found to be almost pure (97.2% pure by GC). The yield of 1,2,2,4,6,6-hexamethyl peridinyl-4-acryamide was 2.17 g (84%).

EXAMPLE 12

Synthesis of 1,2,2,6,6-Pentamethyl Piperidine-4-styrylacetate 1,2,2,6,6-tetramethyl-4-piperidinol (2.5 g, 0.0145 M) was taken in a two necked 50 mL capacity round bottom flask (RB) along with 4-dimethyl aminopyridine (DMAP) (88.5 mg, 0.543 mM) and was kept under nitrogen atomsphere. Dry dichloromethane (30 mL) was injected into the tightly closed RB through the rubber septum, followed by dry triethyl amine (TEA) (2.2 g, 0.0275 M). This reaction mixture was stirred for 20 minutes at room temperature followed by the gradual addition of 3-butenoyl chloride-3-phenyl (styrylacetyl chloride) (0.86 mL, 0.01087 M) with stirring at 0–5° C. initially for 2 hrs. The reaction mixture was then agitated at room temperature for 9 hrs. This reaction mixture was then quenched in ice water, and the product was extracted in dichloromethane (4×25 mL). The combined extract was given (2×20 mL) washes potassium bicarbonate solution and finally dried over anhydrous magnesium sulfate. The solvent was evaporated at 38° C. under vacuum over rotavapor. The product was found to be almost pure (97.2% pure by GC). 1,2,2,6,6-pentamethyl piperidine-4-styrylacetate yielded at the end of the reaction was 3.85 g (81.5%).

The process of the present invention has the edge over other processes by four strong points:

1) The process is an economic, fast and single step process; with very short reaction time.
2) The process comprises of commonly available organic reagents and catalysts, unlike others those who have used expensive and highly unstable organo-metallic catalysts under stringent reaction conditions.
3) High yield (≧80%) can be achieved very easily.
4) Reaction can be carried out via very facile route with very simple and moderate reaction conditions.

What is claimed is:

1. A process for the preparation of a vinylic hindered amine light stabilizer of formula (1)

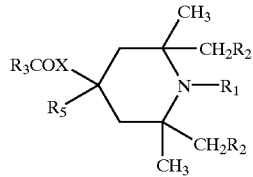
(Formula I)

wherein
$R_1$ is linear or branched $C_1$ to $C_8$ alkyl, alkoxy, alkylphenyl or hydroxy alkyl,
or $R_1$ is allyl, acyl, or cycloalkyl;
$R_2$ is hydrogen or methyl;
$R_3$ is vinyl or $C_{1-4}$ alkyl vinyl;
$R_4$ is hydrogen, $C_{1-4}$ alkyl or alkyl phenyl;
$R_5$ is hydrogen or $C_{1-4}$ alkyl; and
X is O, NH, $C_{1-8}$ linear or branched chain or alkylamino comprising refluxing a solution of a compound of formula II

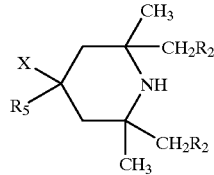
(Formula II)

wherein $R_2$, $R_5$ and X are as defined above, in an organic solvent containing a carbonyl compound of the Formula III $R_1COR_6$   (Formula III)

wherein $R_1$ is as defined above and $R_6$ is linear or branched $C_1$ to $C_8$ alkyl, alkoxy, alkylphenyl or hydroxy alkyl, or $R_1$ is allyl, acyl, or cycloalkyl for a period of from four to six hours, adjusting the pH into the range 7.0 to 9.0, extracting the reaction product in an organic solvent to obtain a compound of Formula IV

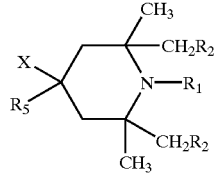
(Formula IV)

and thereafter contacting said compound of Formula IV with an alkyl-substituted aminopyridine or 2-mercaptobezoxazole catalyst in a dry organic solvent and reacting it with a compound of Formula V $CH_2=C(R)-C(O)-Cl$ wherein R is hydrogen, $C_{1-4}$ alkyl or alkylphenyl in an inert atmosphere in the presence of an organic base and thereafter continuing the reaction with stirring for from 8 to 12 hours and then quenching with water to a temperature of from 0 to 4° C. and extracting the product by solvent extraction with an organic solvent and neutralizing the extract with an inorganic base and removing the solvent to obtain a compound of Formula I.

2. A process as claimed in claim 1, wherein the compound of formula II is selected from the group consisting of (2,2,6,6-tetramethyl-4-amino piperidine; 2,2,6,6-tetramethyl-4-piperidinol; 2,2,4,6,6-pentamethyl-4-aminopiperidinol; 2,2,4,6,6-pentamethyl-4-amino piperidine; 2,2,4,6,6-pentamethyl-4-butylamino piperidine and 2,2,6,6-tetramethyl-4-ethyl-4-propyl hydroxy piperidine.

3. A process as claimed in claim 1 wherein the solution of a compound of Formula II used in the reaction between the compounds of Formulae II and III contains an organic acid selected from the group consisting of formic acid, acetic acid and propanoic acid.

4. A process as claimed in claim 1 wherein the carbonyl compound having formula III used is selected from the group consisting of formalin, formaldehyde, acetaldehyde, benzaldehyde, methyl ethyl ketone, methyl benzyl ketone and cyclohexyl methyl ketone.

5. A process as claimed in claim 1 wherein the organic solvent used for extracting the products is selected from the group consisting of diethyl ether, dichloromethane, ethyl acetate and benzene.

6. A process as claimed in claim 1 wherein the catalyst is selected from the group consisting of N,N-dimethyl aminopyridine, 4-aminopyridine and 2-mercaptobenzoxazole.

7. A process as claimed in claim 1 wherein the dry organic solvent used to dissolve the catalyst and compound of Formula IV is selected from the group consisting of dichloromethane, dichloroethane, carbon tetrachloride, cyclohexane, n-hexane and chlorobenzene.

8. A process as claimed in claim 1 wherein the compound of formula V added to react with the compound of formula IV is selected from the group consisting of acryloyl chloride, methacryloyl chloride, pentenoyl chloride and β-butenoyl chloride-3-phenyl.

9. A process as claimed in claim 1 wherein the reaction between the compounds of formulae IV and V is effected in the presence of an aliphatic or aromatic amine selected from the group consisting of triethylamine, trimethylamine, 2,6-lutidine and pyridine.

10. A process as claimed in claim 1 wherein the inorganic base used to neutralize the solvent fraction containing, the product is selected from the group consisting of sodium carbonate, sodium bicarbonate and potassium carbonate.

11. A process as claimed in claim 1 wherein the inert atmosphere used for the reaction of compounds of Formulae IV and V is provided by nitrogen or argon.

* * * * *